United States Patent

Ito et al.

[11] Patent Number: 6,162,833
[45] Date of Patent: *Dec. 19, 2000

[54] PHOTOSTABLE AQUEOUS SOLUTION COMPRISING BENZYL ALCOHOL DERIVATIVES

[75] Inventors: Yasuo Ito; Hideo Kato; Eiichi Koshinaka; Masahiro Yamazaki; Kazuya Matsuo, all of Fukui, Japan

[73] Assignee: Hokuriku Seiyaku Co., Ltd., Fukui, Japan

[*] Notice: This patent is subject to a terminal disclaimer.

[21] Appl. No.: 09/292,664

[22] Filed: Apr. 16, 1999

Related U.S. Application Data

[63] Continuation of application No. 08/983,329, filed as application No. PCT/JP96/01950, Jul. 12, 1996, Pat. No. 5,952,387.

[30] Foreign Application Priority Data

Aug. 4, 1995 [JP] Japan .................... 7-219729

[51] Int. Cl.⁷ .................................. A61K 31/135
[52] U.S. Cl. ................... 514/653; 514/23; 514/25; 514/738; 514/935
[58] Field of Search ................. 514/653, 23, 25, 514/738, 935

[56] References Cited

FOREIGN PATENT DOCUMENTS

| | | |
|---|---|---|
| 0420120 | 4/1991 | European Pat. Off. . |
| 55-43446 | 11/1980 | Japan . |
| 62-277323 | 12/1987 | Japan . |
| 4178356 | 6/1992 | Japan . |
| 7126017 | 5/1995 | Japan . |
| 8-73348 | 3/1996 | Japan . |
| 9101718 | 2/1991 | WIPO . |
| 9425032 | 11/1994 | WIPO . |

OTHER PUBLICATIONS

Copy of the Chemical Abstract No. 125:49312s, vol. 125, No. 5, 1996, p. 150.

Copy of the Chemical Abstract No. 123:93355r, vol. 123, 1995, p. 707.

Copy of the Chemical Abstract No. 109:11744r, vol. 109, 1988, p. 337

Ohki et al., *Encyclopedic Dictionary of Chemistry*, pp. 113, 1338 and 1969 (1989), with English language translations of the terms "alcohol", "Polyhydric alcohol, and Phenolic hydroxy group".

Remington's Pharmaceutical Sciences, pp. 1235, 1254, 1255, and 1264 (1975).

*Primary Examiner*—Rebecca Cook
*Attorney, Agent, or Firm*—Greenblum & Bernstein, P.L.C.

[57] ABSTRACT

Aqueous solution, including at least one of optically active (−)-(R)-α-((tert-butylamino)methyl)-2-chloro-4-hydroxybenzyl alcohol represented by the following formula:

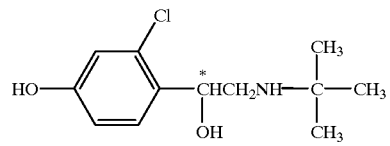

and pharmacologically acceptable salt thereof. The aqueous solution also includes at least one photostabilizer selected from the group consisting of saccharide, sugar alcohol, and polyalcohol. A content of the at least one of optically active (−)-(R)-α-((tert-butylamino)methyl)-2-chloro-4-hydroxybenzyl alcohol and pharmacologically acceptable salt thereof is 0.01 to 10% (w/v) based on a volume of the aqueous solution. A content of the at least one photostabilizer is 1 to 50% (w/v) based on the volume of the aqueous solution. The content of the at least one photostabilizer is at least 10% (w/w) based on a total weight of the at least one of optically active (−)-(R)-α-((tert-butylamino)methyl)-2-chloro-4-hydroxybenzyl alcohol and pharmacologically acceptable salt thereof. Method of making a stabilized aqueous solution.

2 Claims, No Drawings

PHOTOSTABLE AQUEOUS SOLUTION COMPRISING BENZYL ALCOHOL DERIVATIVES

CROSS-REFERENCE TO RELATED APPLICATIONS

This application is a continuation of application Ser. No. 08/983,329, filed Jul. 12, 1996, which is the U.S. National Stage of International Application No. PCT/JP96/01950, Jul. 12, 1996, and claim priority of Japanese Application No. 7-219729, filed Aug. 4, 1995. The entire disclosure of application Ser. No. 08/983,329 is considered as being part of the disclosure of this application, and the entire disclosure of application Ser. No. 08/983,329 is expressly incorporated by reference herein in its entirety.

BACKGROUND OF THE INVENTION

1. Technical Field

The present invention relates to a pharmaceutical composition in the form of an aqueous solution with improved photostability which comprises as an active ingredient a benzyl alcohol compound having excellent stimulating activity on an adrenergic $\beta_2$-receptor and useful as a uterine relaxing agent, bladder relaxing agent and the like.

2. Background Art

Optically active (−)-(R)-α-[(tert-butylamino)methyl]-2-chloro-4-hydroxybenzyl alcohol (hereinafter referred to as "the present compound") represented by the following formula (I):

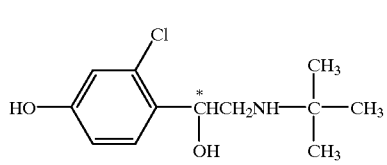

and pharmacologically acceptable salts thereof, which have uterine relaxing activity, bladder relaxing activity and other, have been revealed useful as a therapeutic medicament for threatened premature delivery or a therapeutic medicament for urination disorders such as urinary incontinence, nocturnal enuresis or the like (Japanese Patent Unexamined Publication No. (Hei) 178356/1992).

SUMMARY OF THE INVENTION

For emergent therapy of threatened premature delivery, it is desirable to use an injection by which rapid manifestation of efficacy can be expected. For therapeutic treatment of urination disorder such as urinary incontinence, nocturnal enuresis or the like, which are frequent in the elderly or children, orally applicable liquid formulations are clinically very useful in view of lowered deglutition ability of the elderly and convenient administration to children.

The inventors of the present invention conducted various studies to provide a pharmaceutical composition in the form of an aqueous solution comprising the present compound as an active ingredient. In the course of the studies, they found that the present compound was unstable in an aqueous solution and easily formed decomposed products under irradiation with light, and that an amount of the photodecomposition products tended to be further increased by the addition of a buffering agent required to maintain pH of the solution, e,g., citric acid, acetic acid, L-tartaric acid, D-tartaric acid, or DL-tartaric acid. These findings have not yet been reported so far.

Generally, brown containers for protection from light are used to distribute an aqueous solution for a use as a pharmaceutical composition which contains a photounstable drug as an active ingredient. It was found that the photodecomposition of the present compound was partly prevented by filling an aqueous solution comprising the present compound as an active ingredient in brown containers. However, the results were far from satisfactory from a viewpoint of stability essential to pharmaceutical formulations. The results can be elucidated that light with a relatively short wavelength, i.e., 400 nm or less, is primarily involved in photodecomposition of an ordinary organic compound, and for this reason, brown containers are designed to mainly achieve protection from light having a short wavelength of 400 nm or less, whereas light having a longer wavelength above 400 nm is also involved in the photodecomposition of the present compound, and accordingly, sufficient protection from light cannot be achieved by the brown containers. Therefore, in order to distribute a stable aqueous solution for a use as a pharmaceutical composition which comprises the present compound as an active ingredient, it is necessary to develop a means to achieve higher photostability.

An object of the present invention is to provide a pharmaceutical composition in the form of an aqueous solution having improved photostability which comprises the present compound or a pharmacologically acceptable salt thereof as an active ingredient. In particular, the object of the present invention is to provide a pharmaceutical composition having satisfactory photostability against light of long wavelength which cannot be sufficiently reduced even by using a brown container.

Another object of the present invention is to provide a highly safe photostabilizer which suppresses the photodecomposition of the present compound or a pharmacologically acceptable salt thereof, and can be formulated in a pharmaceutical composition.

The inventors of the present invention made eager efforts to achieve the foregoing objects, and as a result, they found that the photodecomposition of the present compound was remarkably suppressed by the addition of a substance selected from saccharides, sugar alcohols, and polyalcohols to an aqueous solution containing the present compound, and that the photodecomposition of the present compound caused by the light transmitted by a brown container was completely prevented. The present invention was achieved on the basis of these findings. Saccharides, sugar alcohols, and polyalcohols are used as isotonicities or excipients in formulations as pharmaceutical compositions. However, their photostabilizing functions for the present compound has not yet been known.

The present invention thus provides an aqueous solution characterized in that said solution comprises optically active (−)-(R)-α-[(tert-butylamino)methyl]-2-chloro-4- hydroxybenzyl alcohol represented by the following formula (I):

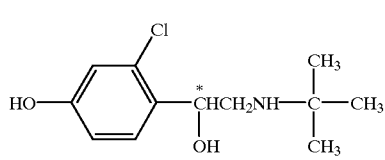

(I)

or a pharmacologically acceptable salt thereof, together with at least one photostabilizer selected from the group consisting of saccharides, sugar alcohols, and polyalcohols.

According to preferred embodiments of the present invention, there are provided the aforementioned solution wherein the saccharide is selected from the group consisting of glucose, sucrose, fructose, and maltose; the aforementioned solution wherein the sugar alcohol is selected from the group consisting of xylitol, sorbitol, and mannitol; the aforementioned solution wherein the polyalcohol is selected from the group consisting of glycerin and propylene glycol; the aforementioned solution wherein a pH is 6.5 or less; the aforementioned solution wherein a content of the optically active (−)-(R)-α-[(tert-butylamino)methyl]-2-chloro-4-hydroxybenzyl alcohol or a pharmacologically acceptable salt thereof is 0.01–10% (w/v) based on a volume of the aqueous solution; the aforementioned solution wherein a content of the photostabilizer selected from the group consisting of saccharides, sugar alcohols, and polyalcohols is 1–50% (w/v) based on a volume of the aqueous solution; and the aforementioned solution which contains 10% (w/w) or more of the photostabilizer based on the total weight of the optical active (−)-(R)-α-[(tert-butylamino)methyl]-2-chloro-4-hydroxybenzyl alcohol or a pharmacologically acceptable salt thereof.

According to another aspect of the present invention, there is provided a photostabilizer selected from the group consisting of saccharides, sugar alcohols, and polyalcohols which suppresses the photodecomposition of the optically active (−)-(R)-α-[(tert-butylamino)methyl]-2-chloro-4-hydroxybenzyl alcohol or a pharmacologically acceptable salt thereof contained in an aqueous solution; and a photostabilized aqueous solutions comprising the optically active (−)-(R)-α-[(tert-butylamino)methyl]-2-chloro-4-hydroxybenzyl alcohol or a pharmacologically acceptable salt thereof together with a substance selected from the group consisting of saccharides, sugar alcohols and polyalcohols.

According to further aspect of the present invention, there is provided a therapeutic medicament for threatened premature delivery or urination disorders which comprises the aforementioned photostabilized solution.

DETAILED DESCRIPTION

The aqueous solution of the present invention is a pharmaceutical composition which can be used as a medicament for oral administration or parenteral administration such as by intravenous injection. The solution is characterized to contain the optically active (−)-(R)-α-[(tert-butylamino) methyl]-2-chloro-4-hydroxybenzyl alcohol or a pharmacologically acceptable salt thereof, together with a substance selected from the group consisting of saccharides, sugar alcohols, and polyalcohols as a photostabilizer for said compound.

The present compound represented by formula (I) can be prepared by, for example, the method described in the Japanese Patent Unexamined Publication No. (Hei) 178356/1992. The pharmacologically acceptable salts of the present compound include, for example, mineral acid salts such as hydrochloride, hydrobromide, hydriodide, nitrate, sulfate, or phosphate, and organic acid salts such as acetate, maleate, fumarate, citrate, oxalate, malate, methanesulfonate, p-toluenesulfonate, mandelate, D-10-camphorsulfonate, L-10-camphorsulfonate, DL-10-camphorsulfonate, L-tartrate, D-tartrate, DL-tartrate, succinate and the like.

A content of the present compound or a pharmacologically acceptable salt thereof in the aqueous solution of the present invention may be 0.01–10% (w/v), preferably 0.02–5% (w/v), and more preferably 0.05–0.5% (w/v) based on the total volume of the solution. The aqueous solution of the present invention may contain one or more of the active ingredients selected from the present compound and pharmacologically acceptable salts thereof.

The photostabilizer has a function to reduce or prevent the photodecomposition of the present compound or a pharmacologically acceptable salt thereof in an aqueous solution. Examples of the saccharides include, for example, glucose, sucrose, fructose, maltose and the like; examples of the sugar alcohols include, for example, xylitol, sorbitol, mannitol and the like; and examples of the polyalcohols include, for example, glycerin, propylene glycol and the like. The aqueous solution of the present invention may contain one or more of these photostabilizers.

The type and amount of the photostabilizer used according to the present invention may be appropriately chosen so as to achieve a desired photostability depending on the type of the active ingredient selected from the present compound or pharmacologically acceptable salts thereof. As a test for the photostability, the method described in Examples of the specification may be employed. For example, 1–50% (w/v), preferably 2–10% (w/v) of the photostabilizer based on the total volume of the aqueous solution may be formulated. The photostabilizer may also be formulated in an amount of 10% (w/w) or more based on a weight of the present compound or a pharmacologically acceptable salt thereof as an active ingredient.

The pH of the aqueous solution of the present invention may preferably be adjusted to 6.5 or lower, most preferably 3–6.5. Acids or bases used for adjusting the pH are not particularly limited so long as they can be added in pharmaceuticals. For example, hydrochloric acid, sodium hydroxide or other may be used. If necessary, a buffering agent such as citric acid, acetic acid, L-tartaric acid, D-tartaric acid, or DL-tartaric acid may be added. Amounts of the buffering agent are not particularly limited, however, it is preferable to add a minimum amount of the buffering agent that is capable of adjusting or maintaining a desired pH. The aqueous solutions of the present invention has a characteristic feature in that the solution is free from photodecomposition of the present compound or a pharmacologically acceptable salt thereof even when the solution is added with a buffering agent such as citric acid, acetic acid, L-tartaric acid, D-tartaric acid, or DL-tartaric acid.

When the aqueous solution of the present invention is used as an injection, the addition of an isotonizer is preferred. However, partial or complete isotonization is sometimes achieved by the photostabilizer contained in the aqueous solution of the present invention, and in that case, it is generally unnecessary to use an entire amount of theoretically-required isotonizer. For example, when glucose or mannitol is used as the photostabilizer in an amount of about 5% (w/v) based on the total volume of the aqueous solution, or when propylene glycol is used in an amount of about 2% (w/v), the aqueous solution is sufficiently isotonized, and therefore, it is generally unnecessary to add an isotonizer.

Methods for preparing the aqueous solution of the present invention are not particularly limited. For example, the solution can be prepared by dissolving, simultaneously or in an appropriate order in purified water or water for injection, respective required amounts of the present compound or a pharmacologically acceptable salt thereof as an active ingredient, the photostabilizer, and other pharmaceutical additives, e.g., a buffering agent, a pH modifier, an isotonizer, an antiseptic, and a soothing agent, if necessary, and then optionally subjecting the resulting solution to a sterilization process such as heat sterilization and sterilization with filtration. As the present compound or a pharmacologically acceptable salt thereof as an active ingredient, any type of known or unknown crystals, or any type of known or unknown hydrates may be used.

EXAMPLES

The present invention will be further detailed by referring to the following examples. However, the scope of the present invention is not limited to these specific examples.

Example 1

| | |
|---|---|
| L-Tartrate of the present compound | 0.2 mg |
| Propylene glycol | 20 mg |
| Citric acid | 0.3 mg |
| Sodium hydroxide | Sufficient quantity |
| Hydrochloric acid | Sufficient quantity |
| Water | Sufficient quantity |
| Total | 1 ml |
| pH | 5.0 |

L-Tartrate of the present compound, propylene glycol, and citric acid were weighed in the ratio according to the aforementioned prescription, and then dissolved in water. The solution was adjusted to pH 5 with sodium hydroxide or hydrochloric acid, and then added with water up to the total volume so as to obtain the prescribed concentrations. The solution was then filled in a brown container and sealed.

Examples 2–20

According to the method of Example 1, solutions of Examples 2–20 were obtained. Prescriptions for these examples are shown in Tables 1–3.

| Example No. | Example 1 | Example 2 | Example 3 | Example 4 |
|---|---|---|---|---|
| L-Tartrate of the present compound | 0.2 mg | 1 mg | 5 mg | 50 mg |
| Photostabilizer | Propylene glycol 20 mg | Propylene glycol 20 mg | Propylene glycol 20 mg | Propylene glycol 20 mg |
| Acid (citric acid) | 0.3 mg | 0.3 mg | 0.3 mg | 0.3 mg |
| Sodium hydroxide | Sufficient quantity | Sufficient quantity | Sufficient quantity | Sufficient quantity |
| Hydrochloric acid | Sufficient quantity | Sufficient quantity | Sufficient quantity | Sufficient quantity |
| Water | Sufficient quantity | Sufficient quantity | Sufficient quantity | Sufficient quantity |
| Total volume | 1 ml | 1 ml | 1 ml | 1 ml |
| pH | 5.0 | 5.0 | 5.0 | 5.0 |
| Osmotic pressure ratio | 1.0 | 1.0 | 1.1 | 2.2 |

| Example No. | Example 5 | Example 6 | Example 7 | Example 8 |
|---|---|---|---|---|
| L-Tartrate of the present compound | 1 mg | 1 mg | 1 mg | 1 mg |
| Photostabilizer | Propylene glycol 20 mg | Propylene glycol 20 mg | Propylene glycol 10 mg | Propylene glycol 100 mg |
| Acid (citric acid) | 0.3 mg | 0.3 mg | 0.3 mg | 0.3 mg |
| Sodium hydroxide | Sufficient quantity | Sufficient quantity | Sufficient quantity | Sufficient quantity |
| Hydrochloric acid | Sufficient quantity | Sufficient quantity | Sufficient quantity | Sufficient quantity |
| Water | Sufficient quantity | Sufficient quantity | Sufficient quantity | Sufficient quantity |
| Total volume | 1 ml | 1 ml | 1 ml | 1 ml |
| pH | 3.0 | 6.5 | 5.0 | 5.0 |
| Osmotic pressure ratio | 1.0 | 1.0 | 0.5 | 5.3 |

| Example No. | Example 9 | Example 10 | Example 11 | Example 12 |
|---|---|---|---|---|
| L-Tartrate of the present compound | 1 mg | 1 mg | 1 mg | 1 mg |
| Photostabilizer | Glucose 47 mg | Sucrose 89 mg | Fructose 47 mg | Maltose 95 mg |
| Acid (citric acid) | 0.3 mg | 0.3 mg | 0.3 mg | 0.3 mg |
| Sodium hydroxide | Sufficient quantity | Sufficient quantity | Sufficient quantity | Sufficient quantity |
| Hydrochloric acid | Sufficient quantity | Sufficient quantity | Sufficient quantity | Sufficient quantity |
| Water | Sufficient quantity | Sufficient quantity | Sufficient quantity | Sufficient quantity |
| Total volume | 1 ml | 1 ml | 1 ml | 1 ml |
| pH | 5.0 | 5.0 | 5.0 | 5.0 |
| Osmotic pressure ratio | 1.0 | 1.0 | 1.0 | 1.0 |

| Example No. | Example 13 | Example 14 | Example 15 | Example 16 |
|---|---|---|---|---|
| L-Tartrate of the present compound | 1 mg | 1 mg | 1 mg | 1 mg |
| Photostabilizer | Xylitol 40 mg | Sorbitol 47 mg | Mannitol 47 mg | Glycerin 25 mg |
| Acid (citric acid) | 0.3 mg | 0.3 mg | 0.3 mg | 0.3 mg |
| Sodium hydroxide | Sufficient quantity | Sufficient quantity | Sufficient quantity | Sufficient quantity |
| Hydrochloric acid | Sufficient quantity | Sufficient quantity | Sufficient quantity | Sufficient quantity |
| Water | Sufficient quantity | Sufficient quantity | Sufficient quantity | Sufficient quantity |
| Total volume | 1 ml | 1 ml | 1 ml | 1 ml |
| pH | 5.0 | 5.0 | 5.0 | 5.0 |
| Osmotic pressure ratio | 1.0 | 1.0 | 1.0 | 1.0 |

| Example No. | Example 17 | Example 18 | Example 19 | Example 20 |
|---|---|---|---|---|
| The present compound | L-Tartrate 1 mg | L-Tartrate 1 mg | 0.6 mg | Hydrochloride 0.7 mg |
| Photostabilizer | Propylene glycol 20 mg | Propylene glycol 20 mg | Propylene glycol 20 mg | Propylene glycol 20 mg |
| Acid | Acetic acid 0.3 mg | L-Tartaric acid 1.0 mg | Citric acid 0.3 mg | Citric acid 0.3 mg |
| Sodium hydroxide | Sufficient quantity | Sufficient quantity | Sufficient quantity | Sufficient quantity |
| Hydrochloric acid | Sufficient quantity | Sufficient quantity | Sufficient quantity | Sufficient quantity |

-continued

| | | | | |
|---|---|---|---|---|
| Water | Sufficient quantity | Sufficient quantity | Sufficient quantity | Sufficient quantity |
| Total volume | 1 ml | 1 ml | 1 ml | 1 ml |
| pH | 5.0 | 5.0 | 5.0 | 5.0 |
| Osmotic pressure ratio | 1.0 | 1.0 | 1.0 | 1.0 |

Comparative Example 1

| | |
|---|---|
| L-Tartrate of the present compound | 1 mg |
| Citric acid | 0.3 mg |
| Sodium hydroxide | Sufficient quantity |
| Hydrochloric acid | Sufficient quantity |
| Water | Sufficient quantity |
| Total | 1 ml |
| pH | 5.0 |

L-Tartrate of the present compound and citric acid were weighed in the ratio according to the aforementioned prescription, and then dissolved in water. The solution was adjusted to pH 5 with sodium hydroxide or hydrochloric acid, and then added with water up to the total volume so as to obtain the above concentrations. The solution was then filled in a brown container and sealed.

Comparative Examples 2–7

According to the method of Comparative Example 1, solutions of Comparative Examples 2–7 were obtained. Prescriptions for these comparative examples are shown in Table 4.

| Comparative Example No. | Comparative Example 1 | Comparative Example 2 | Comparative Example 3 | Comparative Example 4 |
|---|---|---|---|---|
| L-Tartrate of the present compound | 1 mg | 1 mg | 1 mg | 1 mg |
| Additive | — | Sodium chloride 8 mg | Boric acid 19 mg | Sodium hydrogen carbonate 13 mg |
| Acid (citric acid) | 0.3 mg | 0.3 mg | 0.3 mg | 0.3 mg |
| Sodium hydroxide | Sufficient quantity | Sufficient quantity | Sufficient quantity | Sufficient quantity |
| Hydrochloric acid | Sufficient quantity | Sufficient quantity | Sufficient quantity | Sufficient quantity |
| Water | Sufficient quantity | Sufficient quantity | Sufficient quantity | Sufficient quantity |
| Total volume | 1 ml | 1 ml | 1 ml | 1 ml |
| pH | 5.0 | 5.0 | 5.0 | 5.0 |
| Osmotic pressure ratio | 0.03 | 0.9 | 1.1 | 1.1 |

| Comparative Example No. | Comparative Example 5 | Comparative Example 6 | Comparative Example 7 |
|---|---|---|---|
| L-Tartrate of the present compound | 1 mg | 1 mg | 1 mg |
| Additive | Sodium acetate 20 mg | Magnesium chloride 21 mg | Potassium chloride 11 mg |
| Acid (citric acid) | 0.3 mg | 0.3 mg | 0.3 mg |
| Sodium hydroxide | Sufficient quantity | Sufficient quantity | Sufficient quantity |
| Hydrochloric acid | Sufficient quantity | Sufficient quantity | Sufficient quantity |
| Water | Sufficient quantity | Sufficient quantity | Sufficient quantity |
| Total volume | 1 ml | 1 ml | 1 ml |
| pH | 5.0 | 5.0 | 5.0 |
| Osmotic pressure ratio | 1.1 | 1.0 | 1.0 |

Test Example

Photostability test

To examine photostability, each sample sealed in a brown container was stored under irradiation with a fluorescent lamp (3500 luxes, wavelength range: 300–700 nm) at 25° C. for 15 days, and then amounts of decomposed products produced were measured by HPLC. The results are shown in Table 5. From 0.08 to 0.44% of decomposed products were observed in the comparative examples, whereas no decomposition product was observed in the aqueous solutions of the present invention, which verified their excellent photostability.

| Example No. and Comparative Example No. | Decomposed amount under irradiation at 3500 luxes for 15 days (%) |
|---|---|
| Examples 1–20 | N.D. |
| Comparative Example 1 | 0.44 |
| Comparative Example 2 | 0.22 |
| Comparative Example 3 | 0.13 |
| Comparative Example 4 | 0.09 |
| Comparative Example 5 | 0.10 |
| Comparative Example 6 | 0.08 |
| Comparative Example 7 | 0.18 |

N.D.: 0.05% or less

Industrial Applicability

The aqueous solution of the present invention comprising the present compound or a pharmacologically acceptable salt thereof as an active ingredient is stable to light, and has desirable stability as a pharmaceutical preparation. In addition, the photostabilizer added to the aqueous solutions of the present invention is highly safe, and the aqueous solution of the present invention has satisfactory safety as a medicament. Therefore, the aqueous solution is parenterally or orally applicable as a therapeutic medicament for uterine relaxation, bladder relaxation or other.

What is claimed is:

1. 1 An aqueous solution, comprising:
   at least one of optically active (−)-(R)-α-((tert-butylamino)methyl)-2-chloro-4-hydroxybenzyl alcohol represented by the following formula:

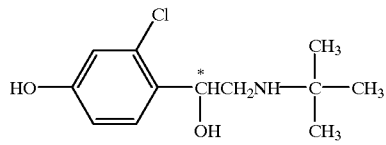

and pharmacologically acceptable salt thereof; and
   at least one photostabilizer selected from the group consisting of saccharide, sugar alcohol, and polyalcohol;
   wherein a content of the at least one photostabilizer is at least 10% (w/w) based on a total weight of the at least one of optically active (−)-(R)-α-((tert-butylamino)methyl)-2-chloro-4-hydroxybenzyl alcohol and pharmacologically acceptable salt thereof.

2. The aqueous solution of claim 1, wherein a content of the at least one of optically active (−)-(R)-α-((tert-butylamino)methyl)-2-chloro-4-hydroxybenzyl alcohol and pharmacologically acceptable salt thereof is 0.01 to 10% (w/v) based on a volume of the aqueous solution.

\* \* \* \* \*